(12) United States Patent
Nikitczuk et al.

(10) Patent No.: US 7,938,256 B2
(45) Date of Patent: May 10, 2011

(54) CONDOM CARD

(75) Inventors: Jason J. Nikitczuk, Belle Mead, NJ (US); Robin Luyber Fernandez, Delran, NJ (US); Michael J. Harrison, Princeton, NJ (US); Richard S. Chomik, Doylestown, PA (US); Salvatore C. Petralia, Buckeye, AZ (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 12/602,972

(22) PCT Filed: Jun. 3, 2008

(86) PCT No.: PCT/US2008/065676
§ 371 (c)(1),
(2), (4) Date: Apr. 27, 2010

(87) PCT Pub. No.: WO2008/151198
PCT Pub. Date: Dec. 11, 2008

(65) Prior Publication Data
US 2010/0206752 A1    Aug. 19, 2010

Related U.S. Application Data

(60) Provisional application No. 60/941,875, filed on Jun. 4, 2007.

(51) Int. Cl.
*B65D 85/08* (2006.01)

(52) U.S. Cl. ...................................................... 206/69

(58) Field of Classification Search ..................... 206/69
See application file for complete search history.

(56) References Cited

U.S. PATENT DOCUMENTS

| | | | |
|---|---|---|---|
| 3,741,377 A | 6/1973 | Krellen | |
| 4,741,434 A * | 5/1988 | Liebman | 206/38 |
| 4,892,188 A * | 1/1990 | Meadows | 206/223 |
| 5,005,695 A | 4/1991 | Tennefos et al. | |
| 5,117,841 A | 6/1992 | McBeth | |
| D345,464 S | 3/1994 | Coronel | |
| 5,316,136 A * | 5/1994 | Castagna | 206/69 |
| 5,427,233 A * | 6/1995 | Zinck et al. | 206/69 |
| 5,551,612 A * | 9/1996 | Hochfeld | 224/219 |
| 5,862,908 A | 1/1999 | Arbin | |
| 5,893,459 A | 4/1999 | Croft | |
| 6,076,661 A * | 6/2000 | Abadi | 206/69 |
| 6,276,549 B1 | 8/2001 | Fasci et al. | |
| 6,612,427 B2 | 9/2003 | Woodhouse | |
| 6,742,521 B2 | 6/2004 | McCleskey et al. | |
| 2001/0035358 A1 * | 11/2001 | Woodhouse | 206/69 |
| 2005/0017059 A1 * | 1/2005 | Salani et al. | 229/72 |
| 2005/0045497 A1 | 3/2005 | Sample | |
| 2007/0083179 A1 | 4/2007 | Fuentes | |

* cited by examiner

*Primary Examiner* — Jacob K Ackun, Jr.
(74) *Attorney, Agent, or Firm* — Frenkel & Associates, P.C.

(57) ABSTRACT

The present invention is directed to a means for storing condoms that will protect and conceal the packaged condoms while they are carried on the person or stored by the consumer subsequent to purchase but prior to use. According to the present invention, the storage means, or condom card, comprises two separable half portions each containing a storage compartment for storing at least one condom therein. The two halves of the condom card are separably attached together by known means in the art, such as juxtaposed tabs and slots.

14 Claims, 6 Drawing Sheets

CONDOM CARD

CROSS-REFERENCE TO RELATED APPLICATION

This application is related to U.S. Provisional Application Ser. No. 60/941,875 filed on Jun. 4, 2007 and claims priority therefrom.

FIELD OF THE INVENTION

The present invention is directed to a packaging device for condoms. More specifically, the present invention is directed to a condom card device which packages two condoms in separable wells.

BACKGROUND OF THE INVENTION

There are various contraceptives available today, but condoms are the most highly recommended prophylactic. The Surgeon General, various public health organizations, colleges and high schools recommend the use of condoms and even advocate free distribution to some degree as a remedy to the current spread of AIDS and venereal disease. However, there is some embarrassment associated with carrying condoms, especially if they fall out of one's wallet, pocket or purse at an inopportune time (as depicted on at least one episode of virtually every television sit-com in the last five years, or in the movie "Broadcast News" when purses had to be inspected by the Secret Service to gain entrance to an embassy party). There has been a long-felt need for a small, sealable pouch in which one or more foil-sealed condoms could be carried or stored to not only protect them against abrasion, but alleviate the anxiety that a condom might be evidenced under most embarrassing circumstances, thereby removing the reason that they are not handy when needed. Such pouch with one condom should be small enough to place in a wallet without adding much bulk, but flexible enough to contain multiple condoms for carrying or storing elsewhere. It should have a releasable, secure, flexible closure. While the primary utility of the pouch is to facilitate carrying condoms on the person, there has also been a long-felt need for such a product in which to store condoms in an automobile or a suitcase or discreetly within reach from one's bed.

Although substantially impermeable to air and moisture, the materials used to package individual condoms are generally thin and lightweight, and the packages must be adapted to be opened by the application of light-to-moderate manual force. Because of this fact, such packages are also susceptible to tearing or puncturing when placed in contact with other articles, such as might occur, for example, when individually packaged condoms are carried or maintained in a pocket, wallet, purse, glove compartment, desk drawer, or the like. Such tearing or puncturing may not be readily apparent to the user, but may be sufficient to permit contamination or degradation of the condom prior to use, or even failure of the condom during use at a subsequent time. One may also lose confidence in the reliability of a condom that has been carried for some time due to the worn or tattered appearance of the package in which it is wrapped, resulting in further anxiety and/or greater potential risk in the event of sexual contact.

The foregoing problems have deterred the effective utilization of condoms in the past, much to the detriment of the general public health. To obviate these problems, means are needed that can hold a single individually packaged condom, or a relatively small number of individually packaged condoms, that will protect the individually packaged condoms prior to use, and that will conceal individually packaged condoms to alleviate embarrassment to an individual carrying the condoms, or to a bystander.

SUMMARY OF THE INVENTION

The present invention is directed to a means for storing condoms that will protect and conceal the packaged condoms while they are carried on the person or stored by the consumer subsequent to purchase but prior to use. According to the present invention, the storage means, or condom card, comprises two separable half portions each containing a receptacle well for storing at least one condom therein. The at least one condom can be individually packaged in a foil, plastic or other similar wrap. The two separable halves are attached together by juxtaposed tabs and slots to form one single condom card.

The condom card also comprises a means of attaching or snapping the two separable half portions together. Any known means for attaching the two separable halves can be used, for example, juxtaposed tabs and slots can be used. In one embodiment, the condom card is covered with a seal or wrapper cover, e.g., a foil-seal or plastic covering, which is releasably secured over each of the receptacle well openings.

DETAILED DESCRIPTION OF THE INVENTION

According to the present invention, a storage means, or condom card, comprises two separable half portions each containing an oval shaped receptacle well for storing at least one condom therein. The two halves can be separably attached by any known means in the art. For example, the two halves can be attached together by juxtaposed tabs and slots forming a single condom card. The tabs and slots are designed so that the card can be snapped apart, resulting in two separate half portions each storing at least one condom therein. The tabs and slots allow for assembly, snapping apart and reassembly of the two halves of the condom card. The at least one condom is covered by a removable cover, such as a foil-seal, plastic seal or other similar seal that can be peeled or otherwise removed from the card.

Figure 1:
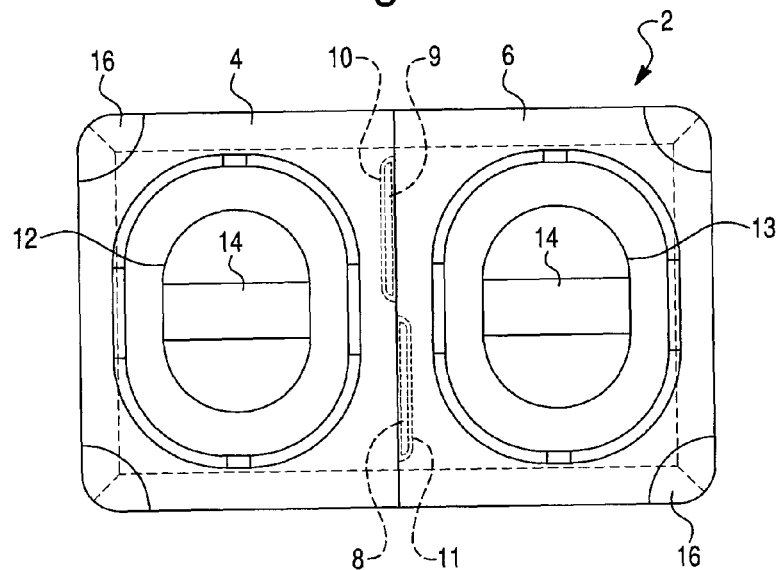
FIG. 1 is a top plan view of the condom card of the present invention, showing two separable halves each having a receptacle well for storing a condom (not show) therein.
Figure 2:
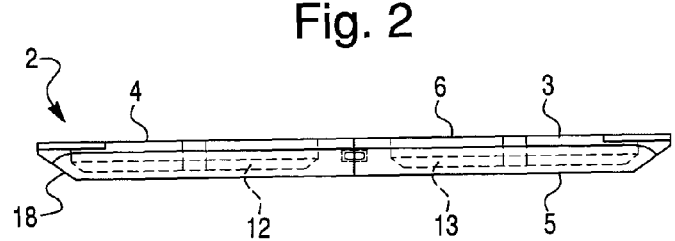
FIG. 2 is a side plan view of the condom card of the present invention.

Referring to FIGS. 1 and 2, a condom card 2 is shown, which comprises a top surface 3 and a bottom surface 5, two separable half portions 4, 6 which can be connected with any known means. For example, to attach the two separable half portions 4, 6, respective tabs 8, 9 and slots 10, 11 attaching means are provided on each of the two separable half portions 4, 6. The tab 8 from one half portion 4 aligns with the slot 11 on a second half portion 6. As shown, two tab and slot attaching means are provided which attach or snap together the two separable half portions 4, 6 to hold the two halves 4, 6 together as a single condom card 2. The two half portions 4, 6 can then be separated by snapping the two separable half portions 4, 6 apart, releasing the respective tabs 8, 9 from the juxtaposed slots 10, 11 of the adjacent half portions.

The two half portions 4, 6 each contain respective oval shaped receptacle wells 12, 13 for storing a condom (not shown) therein. As shown, the center portion 14 of oval shaped receptacle wells 12, 13 can be raised. The oval shaped receptacle wells 12, 13 in each half portion 4, 6 can be covered with a releasable cover (not shown), which is typically a foil-seal or wrapper covering the oval shaped receptacle well opening. The condom card 2 also contains corner recesses 16, which allow for easy removal of the cover portion (not shown) covering each of the oval shaped receptacle wells 12, 13.

In one embodiment, at least one non-wrapped condom is placed in each of the oval shaped receptacle wells 12, 13. In another embodiment, at least one condom is wrapped in a foil, plastic, or other like wrapping before being placed within the oval shaped receptacle wells 12, 13. The releasable cover (not shown) seals at least one condom into the oval shaped receptacle wells 12, 13.

FIG. 2 shows a side plan view of the condom card 2. As shown, the condom card 2 contains a top surface 3, a bottom surface 5, and beveled edges 18 on the bottom surface 5 of the condom card 2.

Figure 3:
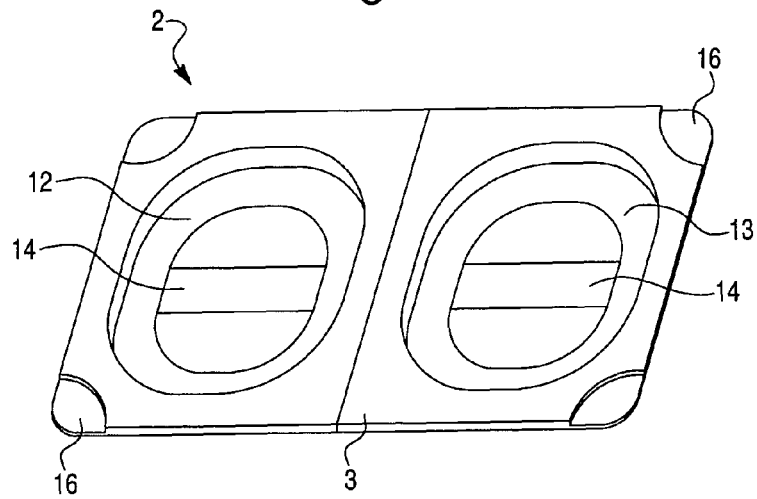
FIG. 3 is a top perspective view of the condom card of the present invention.

FIG. 3 shows a top perspective view showing the top surface 3 of the condom card 2. As shown, the top surface 3 has two oval shaped receptacle wells 12, 13 for storing at least one condom therein. The center portion 14 of each of the oval shaped receptacle wells 12, 13 can be raised. The condom card 2 also shows corner recesses 16, which allow for easy removal of the cover (not shown) covering each of the oval shaped receptacle wells 12.

Figure 4:
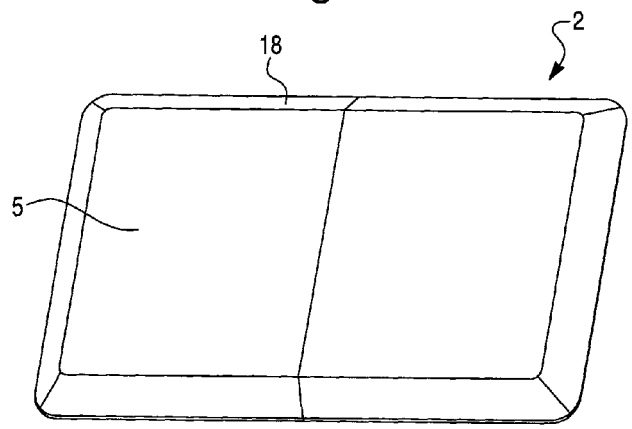
FIG. 4 is a bottom perspective view of the condom card of the present invention.

FIG. 4 shows a bottom perspective view showing the bottom surface 5 of the condom card 2. As shown, the bottom surface 5 contains beveled edges 18 on all four edges of the bottom surface 5 of the condom card 2.

Figure 5:
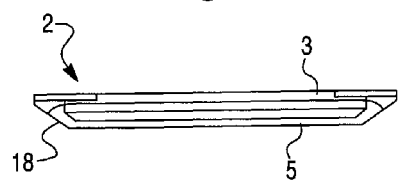
FIG. 5 is an end plan view of the condom card of the present invention.

FIG. 5 shows an end plan view of the condom card. As shown, the condom card 2 contains beveled edges 18 on the bottom surface of the condom card 2. Again, the oval shaped receptacle wells 12, 13 in each half portion 4, 6, as shown in FIGS. 1-3 and 5, can be covered with a releasable cover (not shown), which is typically a foil-seal or wrapper covering the oval shaped receptacle well opening. In another embodiment, the half portions 4, 6, as shown in FIGS. 1-5, can each be covered with a releasable cover (not shown), which can be, for example, a foil-seal or wrapping.

Figure 6:
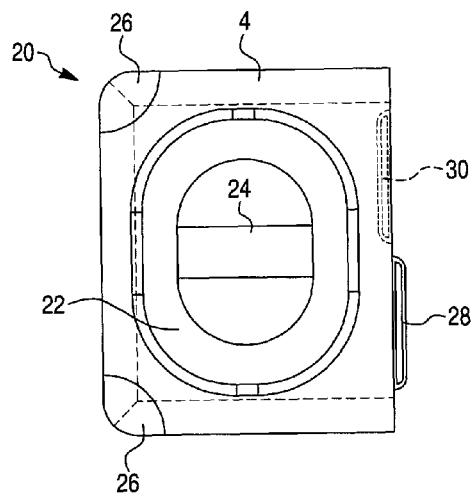
FIG. 6 is a top plan view of one half portion of the condom card of the present invention having a receptacle well for storing a condom (not show) therein.
Figure 7:
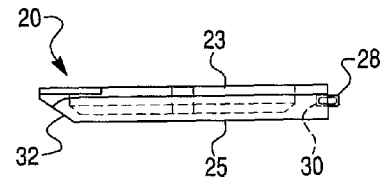
FIG. 7 is a side plan view of a single half portion of the condom card of the present invention.

As shown in FIGS. 6 and 7, one half portion 20 of the condom card of the present invention comprises a top surface 23, a bottom surface 25 and an oval shaped receptacle well 22 for storing a condom (not shown) therein. The half portion 20 also shows a means 28, 30 for connecting the half portion 20 with a second adjacent half portion (not shown). Typically, any known means for attaching the two half portions can be used. As shown, one means for attaching adjacent half portions is a tab 28 and slot means 30. The tab 28 from one half portion 20 aligns with the slot of a second half portion (not shown). Likewise, the tab from the second half portion (not shown) aligns with the slot 30 of half portion 20. The tab 28 and slot 30 attaching means allow for the two separable half portions to be snapped together to form one condom card.

The half portion 20 contains an oval shaped receptacle well 22 for storing a condom (not shown) therein. As shown, the center portion 24 of the oval shaped receptacle well 22 can be raised. The oval shaped receptacle well 22 can be covered with a releasable seal or wrapper cover (not shown), which is typically a foil-seal or wrapper covering the oval shaped receptacle well 22 opening. The half portion 20 also contains corner recesses 26, which allow for easy removal of the cover (not shown) covering the oval shaped receptacle well 22.

In one embodiment, at least one non-wrapped condom is placed in the oval shaped receptacle well 22. In another embodiment, at least one condom is wrapped in a foil, plastic, or other like wrapping before being placed within the oval shaped receptacle well 22. A releasable cover (not shown) seals at least one condom into the oval shaped receptacle well 22.

FIG. 7 shows a side plan view of one half portion 20 of the condom card of the present invention. As shown, the half portion 20 contains a top surface 23, a bottom surface 25, a beveled edge 32 and a tab 28 and slot 30 for attaching or snapping the half portion 20 together with a second half portion (not shown).

Figure 8:
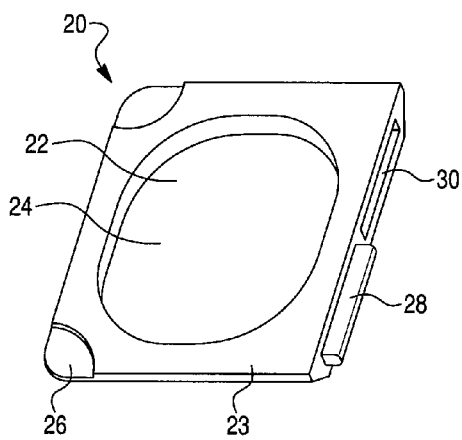
FIG. 8 is a top perspective view of a single half portion of the condom card of the present invention.

FIG. 8 shows a top perspective view showing the top surface 23 of one half portion 20 of the condom card of the present invention. As shown, the top surface 23 has an oval shaped receptacle well 22 for storing at least one condom therein. The center portion 24 of the oval shaped receptacle well 22 can be raised. The half portion 20 also contains corner recesses 26, which allow for easy removal of the cover (not shown) which covers the oval shaped receptacle well 22.

Figure 9:
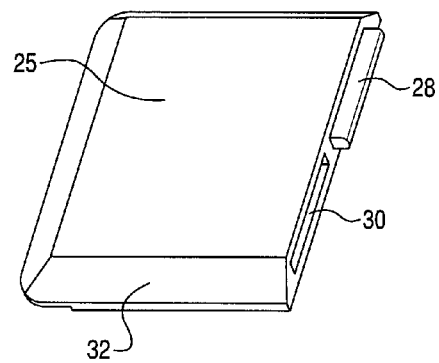
FIG. 9 is a bottom perspective view of a single half portion of the condom card of the present invention.

FIG. 9 shows a bottom perspective view showing the bottom surface 25 of one half portion 20 of the condom card of the present invention. As shown, the bottom surface 25 contains beveled edges 32 on all four edges of the bottom surface 25 of the half portion 20. Also shown are tab 28 and slot 30 attaching means.

Figure 10:
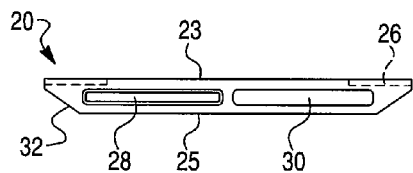
FIG. 10 is an end plan view of a single half portion of the condom card of the present invention showing means for attachment and separability.

FIG. 10 shows an end plan view of one half portion 20 of the condom card of the present invention. As shown, the half portion 20 contains a top surface 23, bottom surface 25, beveled edges 32, and tab 28 and slot 30 attaching means. The oval shaped receptacle well 22 of half portion 20, as shown in FIGS. 6-10, can be covered with a releasable cover (not shown), which is typically a foil-seal or wrapper covering the oval shaped receptacle well opening. In another embodiment, the entire half portion 20, as shown in FIGS. 6-10, can be covered with a releasable cover (not shown), which can be, for example, a foil-seal or wrapping.

Figure 11:
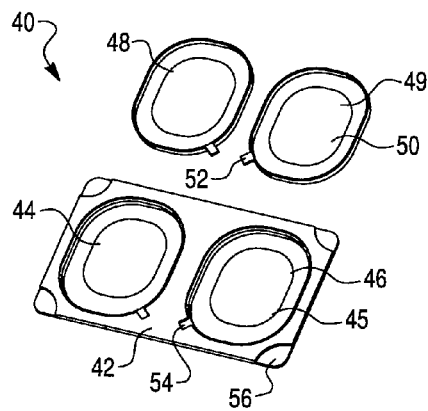
FIG. 11 is a top perspective view of a so-called butter cup design variant, wherein the cups sit in wells to prevent lubricant from covering the card.

FIG. 11 is a top perspective view of a so-called butter cup design variant, wherein the butter cups sit in wells to prevent lubricant from covering the card, another embodiment of the present invention. FIG. 11 shows a condom card 40, which comprises a top surface 42 and a bottom surface (not shown), and two oval shaped receptacle wells 44, 45. In one embodiment, the condom card 40 can comprises two separable half portions (not shown), which can be snapped apart, in accordance with this invention. In accordance with this embodiment, the two separable half portions are attached together by juxtaposed tabs and slots (not shown) to form one single condom card 40. As shown, the center portion 46 of the oval shaped receptacle wells 44, 45 can be raised. The condom card 40 also contains corner recesses 56, which allow for easy removal of a cover (not shown) covering each of the oval shaped receptacle wells 44, 45. As previously pointed out, the cover (not shown) of the condom card 40 can be a seal or wrapper cover, e.g., a foil-seal or plastic covering, which is releasably secured over each of the receptacle well openings 44, 45, and/or covering each half portion (not shown) of the condom card 40. The condom card of this embodiment further comprises two cups 48, 49, which sit in receptacle wells 44, 45 to prevent any excess lubricant from covering, and potentially damaging the card 40. The two cups 48, 49 are also oval shaped, thereby matching the oval shape of the oval shaped receptacle wells 44, 45 and allowing the two cups 48, 49 to fit securely within the receptacle wells 44, 45. In one embodiment a means 52, 54 can be provided which prevents the two cups 48, 49 from freely moving within the oval shaped receptacle wells 44, 45. For example, the two cups 48, 49 can have a tab 52, which fits into a corresponding notch 54 on the condom card 40, thereby preventing each of the two cups 48, 49 from freely moving within the oval shaped receptacle wells 44, 45. The center portion 50 of the two cups 48, 49 can be raised to match the raised center portion 46 of the oval shaped receptacle wells 44, 45.

Figure 12:
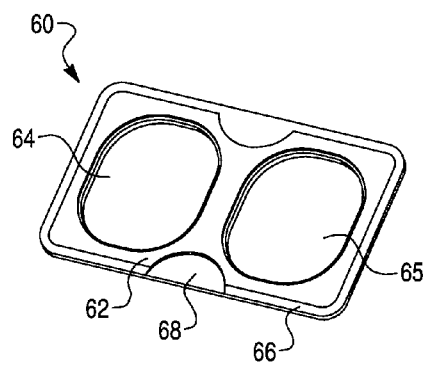
FIG. 12 is a top perspective view of an open variant, wherein both the top and bottom portions are closed with film or foil.

FIG. 12 is a top perspective view of an open well variant, wherein both the top and bottom of the condom card can be closed with film or foil. FIG. 12 shows a condom card 60, which comprises a top surface 62 and a bottom surface (not shown), and two oval shaped receptacle holes 64, 65, which run through the condom card 60. In accordance with this embodiment, the bottom surface of the condom card 60 can be covered or closed with a film or foil, at least one condom (not shown) placed into the oval shaped receptacle holes 64, 65, and subsequently the top surface 62 covered or closed with a second film or foil. The condom card 60 may also contain side recesses 68, which allow for easy removal of the cover portion (not shown) covering each of the oval shaped receptacle wells 64, 65, and beveled edges 66. In another embodiment, the condom card 60 can comprises two separable half portions (not shown), which can be snapped apart, in accordance with this invention. In accordance with this embodiment, the two separable half portions are attached together by juxtaposed tabs and slots (not shown) to form one single condom card 60.

Figure 13:
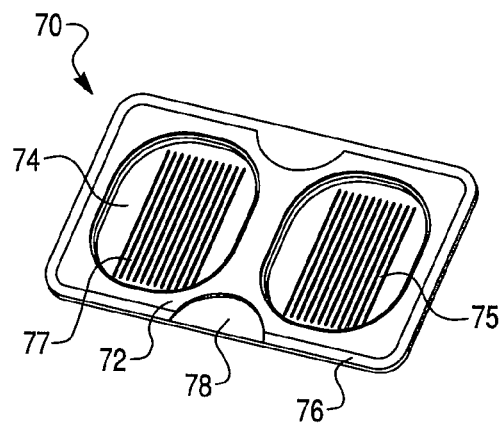
FIG. 13 is a top perspective view of a variant wherein the bottom of the receptacle contains slits adapted to contain lubricant.

FIG. 13 is a top perspective view of a variant wherein the bottom of the receptacle contains slits adapted to contain lubricant. FIG. 13 shows a condom card 70, which comprises a top surface 72 and a bottom surface (not shown), and two oval shaped receptacle wells 74, 75. In one embodiment, the condom card 70 can comprises two separable half portions (not shown), which can be snapped apart, in accordance with this invention. In accordance with this embodiment, the two separable half portions are attached together by juxtaposed tabs and slots (not shown) to form one single condom card 70. As shown, the two oval shaped receptacle wells 74, 75 can contain therein a plurality of slits or channels 77. The slits or channels 77 help to catch any excess lubricant preventing any excess lubricant from covering, and potentially damaging the card 70. The condom card 70 may also contain side recesses 78, which allow for easy removal of the cover portion (not shown) covering each of the oval shaped receptacle wells 74, 75, and beveled edges 76.

Figure 14:
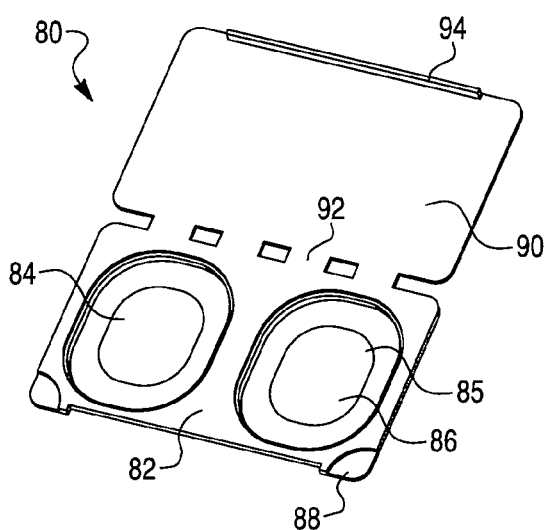
FIG. 14 is a top perspective view showing a variant wherein a solid lid closes to form a clamshell.

FIG. 14 is a top perspective view showing a variant wherein a solid lid closes to form a clamshell. FIG. 14 shows a condom card 80, which comprises a top surface 82 and a bottom surface (not shown), and two oval shaped receptacle wells 84, 85. As shown, the center portion 86 of oval shaped receptacle wells 84, 85 can be raised. The condom card 80 also contains corner recesses 88, which allow for easy opening of a solid lid 90 that closes over top of the oval shaped receptacle wells 84, 85. The solid lid 90 further comprises a flexible means 92 for attaching the solid lid 90 to the condom card 80 and a lip 94 on the solid lid 90, which enables the solid lid 90 to snap shut over top of the oval shaped receptacle wells 84, 85 of the condom card 80. The flexible means can be a single piece of flexible plastic attaching the condom card 80 and the solid lid 90, or as shown, a plurality of flexible plastic pieces 93 attaching the condom card 80 and the solid lid 90.

Figure 15:
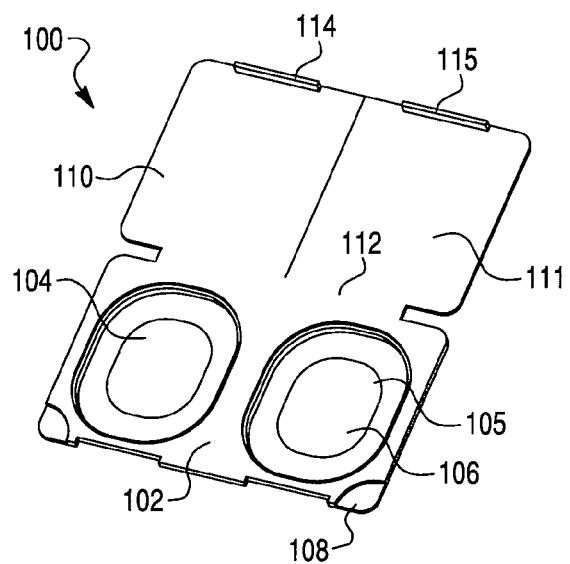
FIG. 15 is a top perspective view depicting a condom card container similar to that depicted in FIG. 14, with the clamshell being split in two.

FIG. 15 is a top perspective view depicting a condom card container similar to that depicted in FIG. 14, with the clamshell lid being split in two. FIG. 15 shows a condom card 100, which comprises a top surface 102 and a bottom surface (not shown), and two oval shaped receptacle wells 104, 105. As shown, the center portion 106 of oval shaped receptacle wells 104, 105 can be raised. The condom card 100 also contains corner recesses 108, which allow for easy opening of separate solid lids 110, 111, which closes over top of the oval shaped receptacle wells 84, 85, respectfully. The solid lids 110, 111 further comprise a flexible means 112 for attaching the solid lids 110, 111 to the condom card 102 and a lip 114, 115 on the solid lid, 110, 111, which enables the solid lids 110, 111 to snap shut over top of each of the oval shaped receptacle wells 104, 105, respectfully, of the condom card 100. In general, any flexible means may be used, for example, as shown, a single piece of flexible plastic 112, which attaches the solid lids 110, 111 to the condom card 100. In another embodiment, the condom card 100 can comprises two separable half portions (not shown), which can be snapped apart, in accordance with this invention. In accordance with this embodiment, the two separable half portions are attached together by juxtaposed tabs and slots (not shown) to form one single condom card 100.

Figure 16:
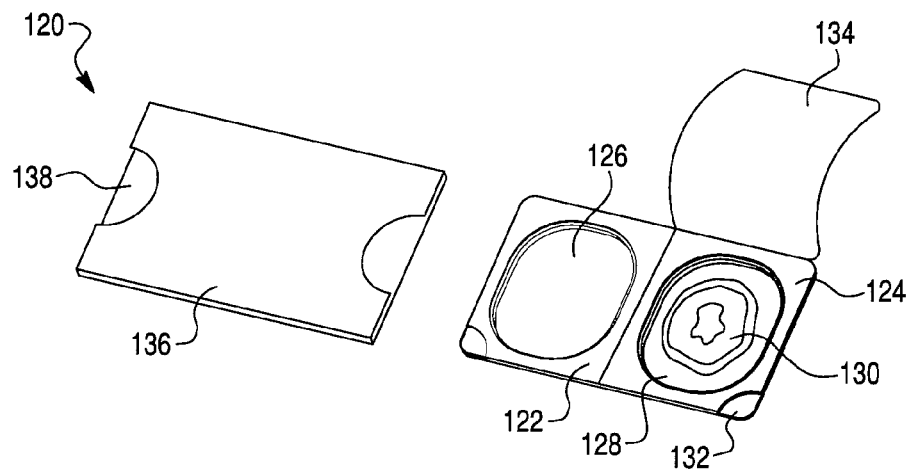
FIG. 16 is a top plan view of a packaging variation wherein the condom card container is fit into a sleeve.

FIG. 16 is a top plan view of a packaging variation wherein the condom card container is fit into a sleeve. FIG. 16 shows a condom card 120, which comprises a top surface 122 and a bottom surface (not shown), and two oval shaped receptacle wells 126, 128 formed in the top surface 122. In one embodiment, the condom card 120 can comprises two separable half portions (not shown), which can be snapped apart, in accordance with this invention. In accordance with this embodiment, the two separable half portions are attached together by juxtaposed tabs and slots (not shown) to form one single condom card 120. In another embodiment, the center portion (not shown) of oval shaped receptacle wells 126, 128 can be raised. The condom card 120 may also contain a break-away corner portion 132 of the top surface of the condom card 120, to assist in easy removal of a cover portion 134, which covers each of the oval shaped receptacle wells 126, 128. In another embodiment, the condom card 120 may contain corner recesses (not shown), which allow for easy removal of the cover portion 134 covering each of the oval shaped receptacle wells 126, 128. As previously pointed out, the cover portion 134 of the condom card 120 can be a seal or wrapper cover, e.g., a foil-seal or plastic covering, which is releasably secured over each of the receptacle well openings 126, 128. Furthermore, as shown in FIG. 16, the condom card 120 of this embodiment can comprise a sleeve covering 136, which forms a removable protective covering over the condom card 120. The condom card 120 can be easily removed from the sleeve 136 by sliding the condom card out of the sleeve 136, or vice versa, by sliding the sleeve off from the condom card 120. An open notch 138 can be provided, at one or both ends of the sleeve 132, to improve the user's ability to remove the sleeve 136 from the condom card 120. In one embodiment, the sleeve is open at both ends, and thus, can be removed from the condom card 120 by sliding the sleeve 136 off the condom card in either direction. In another embodiment, the sleeve 136 is open only at one end, providing better protection to the condom card 120. The sleeve 136 can be made of any suitable material, for example, the sleeve 136 can be made of paper, cardboard, plastic, etc.

Figure 17:
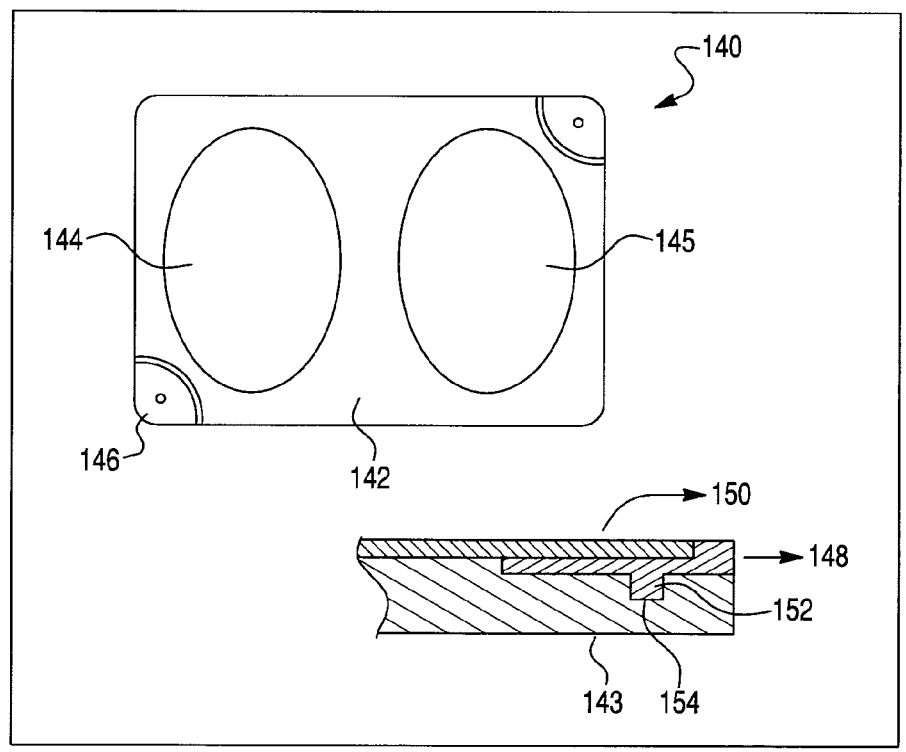
FIG. 17 is a top plan view showing a condom card container such as the container depicted in FIG. 1, wherein the corners include snap tabs.

FIG. 17 is a top plan view showing a condom card container such as the container depicted in FIG. 1, wherein the corners include snap tabs. FIG. 17 shows a condom card 140, which comprises a top surface 142 and a bottom surface (not shown), and two oval shaped receptacle wells 144, 145. In one embodiment, the condom card 140 can comprises two separable half portions (not shown), which can be snapped apart, in accordance with this invention. In accordance with this embodiment, the two separable half portions are attached together by juxtaposed tabs and slots (not shown) to form one single condom card 140. The condom card 140 also contains snap tabs 146, allowing for easy removal, and re-positioning or re-sealing of the cover portion (not shown), which covers each of the oval shaped receptacle wells 144, 145. In one embodiment, the cover portion 150 is permanently affixed to the snap tabs 146, for example, the cover portion can be glued into place on the snap tabs 146. The snap tabs 146 can then be snapped into place on the corners of the condom card 140 with the use of a tab portion 152 and corresponding slot 154 means, which can be used to snap the snap tab 146 to the condom card 140. In this embodiment, the tab portion 152 is snapped into a corresponding slot 154 in the top surface 142 of the condom card 140. In another embodiment, the snap tabs 146 contain a sticky substance thereon which allows the cover portion 150 to stick to the snap tabs 146, thereby sealing the oval shaped receptacle wells. Alternatively, the corners of the cover portion 150 can contain a sticky substance, for example an adhesive, which allows the cover portion 150 to adhere to the snap tabs. As previously pointed out, the cover portion 150 of the condom card 140 can be a seal or wrapper cover, e.g., a foil-seal or plastic covering, which is releasably secured over each of the receptacle well openings 144, 145 using the snap tabs 148 of this embodiment.

Figure 18:
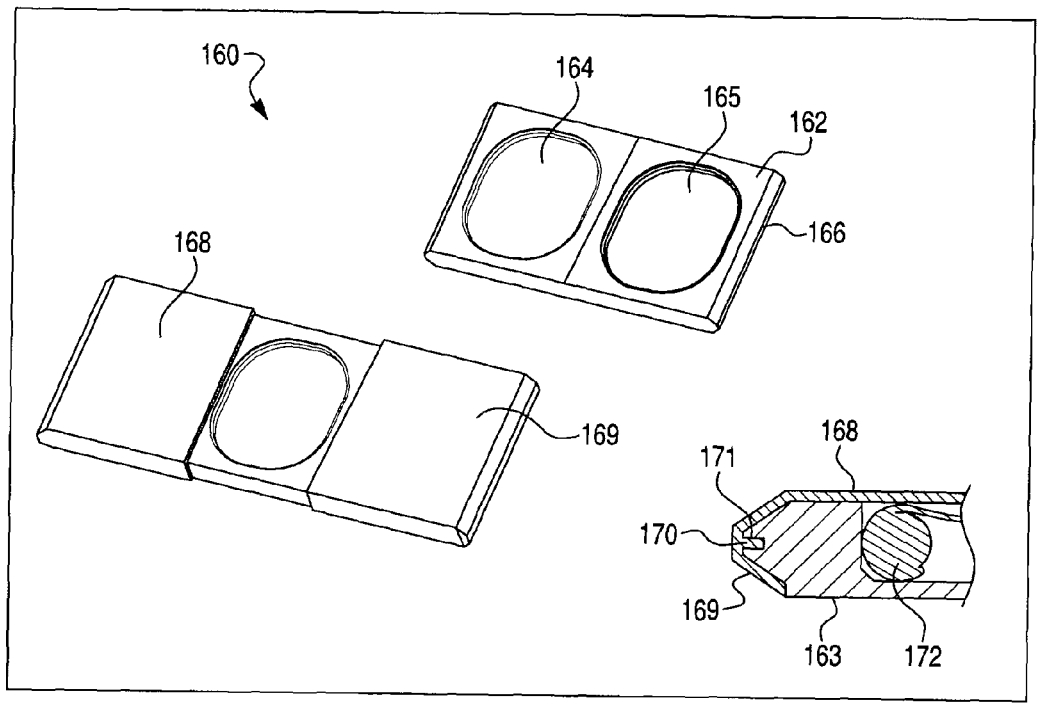
FIG. 18 is a top perspective view depicting a condom card container such as the container depicted in FIG. 1 wherein the container includes a sliding lid.

FIG. 18 is a top perspective view depicting a condom card container such as the container depicted in FIG. 1 wherein the container includes a sliding lid. FIG. 18 shows a condom card 160, which comprises a top surface 162 and a bottom surface 163, and two oval shaped receptacle wells 164, 165. In one embodiment, the condom card 160 can comprises two separable half portions (not shown), which can be snapped apart, in accordance with this invention. In accordance with this embodiment, the two separable half portions are attached together by juxtaposed tabs and slots (not shown) to form one single condom card 160. Also, in accordance with this embodiment, the condom card 160 further comprises two slidable covers 168, 169, which can be slide over the oval shaped receptacle wells 164, 165 to close the condom card and protect the at least one condom 172 contained therein. The slidable covers 168, 169 can also be slide toward the ends of the condom card 160 to uncover or open the condom card 160. As shown, the slidable cover can contain a tab 170 that snaps into a corresponding slot 171 on the end of the condom card 160, thereby snapping the slidable cover 168 into a closed position over top of the oval shaped receptacle wells 164, 165, and preventing the slidable cover 168 from freely sliding to an open position. In one embodiment, the condom card 160 includes one or more beveled edges 166. The beveled edge 166 can be on the top surface 162 or bottom surface 163 of the condom card, or both. In an alternative embodiment, the condom card 160 has a beveled edge 166 on both the top surface 162 and bottom surface 163 of both ends of the condom card 160. In yet another embodiment, the ends of the slidable covers 168, 169 can be formed in a manner which corresponds to the beveled edge 166 on both the top surface 162 and bottom surface 163 of the condom card 160. As previously pointed out, the condom card 160 of this embodiment may further contain a seal or wrapper cover (not shown), e.g., a foil-seal or plastic covering, which is releasably secured over each of the oval shaped receptacle wells 164, 165, and located underneath of the slidable covers 168, 168 when they are closed.

Figure 19:
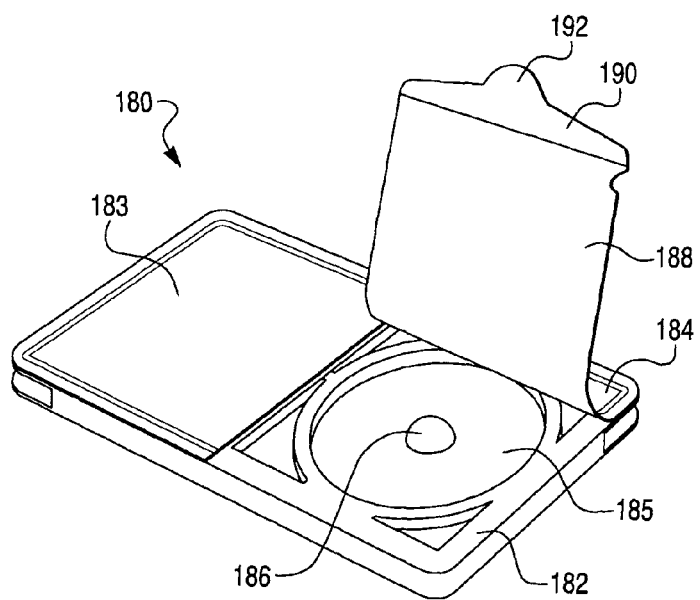
FIG. 19 is a top perspective view depicting a condom card container similar to that depicted in FIG. 1, but further including features such as a raised portion for aid in condom removal.

FIG. 19 is a top perspective view depicting a condom card container similar to that depicted in FIG. 1, but further including features such as a raise portion for aid in condom removal. FIG. 19 shows a condom card 180, which comprises a top surface 182 and a bottom surface (not shown), two half portions 183, 184 and two oval shaped receptacle wells 185. The two separable half portions may be attached together by juxtaposed tabs and slots (not shown) to form one single condom card 160. As shown, the center portion 186 of oval shaped receptacle well 185 can be raised to aid in condom removal. In accordance with this embodiment, the condom card 180 contains a seal or wrapper covering 188, e.g., a foil-seal or plastic covering, which is releasably secured over each of the oval shaped receptacle wells 185. The covering 188 can further contain an adhesive strip 190 or sticker on the underside of the said covering 188, which allows the covering 188 to be re-sealed to the top surface of the condom card 180 over the oval shaped receptacle wells 185, and a tab portion 192 which aids in pealing back the covering 188 to open the condom card.

What is claimed is:

1. A condom card comprising:
    a generally flat rectangular card body defining two separable half portions each half portion having a top surface and a bottom surface and an oval-shaped cavity therein on said top surface;
    at least one condom fitting into each of said oval-shaped cavities; and a removable cover placed over said oval-shaped cavities;
    wherein said two separable half portions further comprise corresponding tabs and slots for snapping said two half portions together.

2. The condom card of claim 1, wherein said removable cover is perforated between said two separable half portions such that said separable half portions can be snapped apart and each of said separable half portions remaining covered by one-half of said removable cover.

3. The condom card of claim 1, wherein each of said oval-shaped cavities contains one condom.

4. The condom card of claim 3, wherein said condoms are individually wrapped.

5. The condom card of claim 1, wherein said condom card further comprises one or more beveled edges.

6. The condom card of claim 5, wherein said one or more beveled edges are on said bottom surface of said condom card.

7. The condom card of claim 1, wherein said condom card further comprises at least one corner recess on each of said separable half portions which allows for easy removal of said removable cover.

8. The condom card of claim 1, wherein said condom card further comprises at least one oval-shaped cup contained within said oval-shaped cavities.

9. The condom card of claim 1, wherein said condom card further comprises a plurality of channels at the bottom of said oval-shaped cavities.

10. The condom card of claim 1, wherein said condom card further comprises a protective sleeve covering.

11. The condom card of claim 1, wherein said removable cover can be re-sealed.

12. The condom card of claim 11, wherein said condom card further contains snap corners which allows for said removable cover to be unsnapped to remove at least one said condom from said condom card, and re-snapped to re-seal said condom card.

13. The condom card of claim 11, wherein said condom card further contains at least one slidable cover.

14. The condom card of claim 11, wherein said removable cover further contains an adhesive on an underside of said removable cover, said adhesive allowing for said removable cover to be re-sealed to said top surface of said condom card.

* * * * *